United States Patent [19]

Pretzer et al.

[11] 4,339,611
[45] Jul. 13, 1982

[54] PROCESS FOR SELECTIVE FORMATION OF C₄ COMPOUNDS AND ORGANIC SULFIDE-CONTAINING CATALYST SYSTEM USED THEREIN

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[21] Appl. No.: 215,556

[22] Filed: Dec. 11, 1980

[51] Int. Cl.³ .................... C07C 27/22; C07C 45/50
[52] U.S. Cl. ................................ 568/487; 568/888; 568/902
[58] Field of Search ............... 568/487, 888, 449, 902

[56] References Cited

U.S. PATENT DOCUMENTS

| | | | |
|---|---|---|---|
| 2,623,906 | 12/1952 | Gresham | 260/615 |
| 3,248,432 | 4/1966 | Riley et al. | 260/638 |
| 3,285,948 | 11/1966 | Butter | 260/642 |
| 3,387,043 | 6/1968 | Kuraishi et al. | 568/902 |
| 4,133,966 | 1/1979 | Pretzer et al. | 568/902 |
| 4,171,461 | 10/1979 | Bartish | 568/902 |
| 4,205,190 | 5/1980 | Gane et al. | 568/902 |
| 4,239,704 | 12/1980 | Pretzer et al. | 568/487 |
| 4,262,154 | 4/1981 | Gane et al. | 568/902 |

Primary Examiner—Werren B. Lone

Attorney, Agent, or Firm—Deane E. Keith; Forrest D. Stine; Joseph J. Carducci

[57] ABSTRACT

C₄ compounds including n-butanol and n-butanal are produced by reacting methanol, hydrogen, and carbon monoxide, in the presence of a cobalt catalyst selected from the group consisting of (a) a cobalt carbonyl, (b) a hydrido cobalt carbonyl and (c) a cobalt-containing material convertible to a cobalt carbonyl or a hydrido cobalt carbonyl, an iodine promotor and an organic sulfide having the formula:

$$R_1-S-R_2$$

wherein $R_1$ and $R_2$ can be the same or different members selected from the group consisting of saturated or unsaturated, straight or branched chain alkyl radicals having from one to 24 carbon atoms, cycloalkyl radicals having from three to 40 carbon atoms, aryl radicals having from six to 20 carbon atoms, aralkyl and alkaryl radicals having from six to 40 carbon atoms and halogen substituted derivatives thereof. A high degree of selectivity towards the formation of butanol and butanal is provided by using the cobalt entity and the organic sulfide in a molar ratio in the range of about 2:1 to about 1:10, based on elemental cobalt and sulfur. The reaction is conducted at elevated temperature and pressure conditions for a time sufficient to convert methanol to n-butanol and n-butanal.

16 Claims, No Drawings

PROCESS FOR SELECTIVE FORMATION OF C$_4$ COMPOUNDS AND ORGANIC SULFIDE-CONTAINING CATALYST SYSTEM USED THEREIN

CROSS-REFERENCE TO RELATED APPLICATIONS

Reference is made to the following U.S. applications filed on even date, which are incorporated by reference:

U.S. patent application Ser. No. 215,555 to Wayne R. Pretzer, Thaddeus P. Koblyinski and John E. Bozik entitled "Process for Selective Formation of C$_4$ Compounds Using Thiol-Containing Catalyst System".

U.S. patent application Ser. No. 215,554 to Wayne R. Pretzer, Thaddeus P. Koblyinski and John E. Bozik entitled "Process for Selective Formation of C$_4$ Compounds Using Biphosphine Disulfide-Containing Catalyst System".

U.S. patent application Ser. No. 215,354 to Wayne R. Pretzer, Thaddeus P. Koblyinski and John E. Bozik entitled "Process for Selective Formation of C$_4$ Compounds Using Tertiary Organo Group VA Compound-Containing Catalyst System".

FIELD OF THE INVENTION

The present invention relates to a process for selectively producing C$_4$ compounds comprising n-butanol and n-butanal, and to the catalyst system used in such process. More particularly, the invention relates to the production of C$_4$ products by the interaction of methanol, hydrogen and carbon monoxide in the presence of a cobalt catalyst, an iodine promoter and an organic sulfide component wherein the molar ratio of cobalt to sulfide components can be controlled to provide a catalyst system highly selective to the production of C$_4$ products.

DESCRIPTION OF THE PRIOR ART

The reaction of methanol with hydrogen and carbon monoxide to produce ethanol is well known. Generally, such processes produce a wide spectrum of compounds in addition to ethanol including other alcohols, as well as ketones, carboxylic acids and the like.

Thus, for example, U.S. Pat. No. 3,285,948 entitled "Halides of Ruthenium and Osmium in conjunction with Cobalt and Iodine in the Production of Ethanol from Methanol" to G. N. Butter teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, I$_2$, or alkali metal iodides along with a secondary promoter, i.e., ruthenium halide or osmium halide.

Another process is set forth in U.S. Pat. No. 3,248,432, entitled "Process for the Production of Ethyl Alcohol," to A. D. Riley et al which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 4,133,966 to W. R. Pretzer et al entitled "Selective Formation of Ethanol from Methanol, Hydrogen and Carbon Monoxide" discloses contacting methanol, hydrogen and carbon monoxide with a catalyst system containing cobalt acetylacetonate, a tertiary organo Group VA compound of the Periodic Table, an iodine compound and a ruthenium compound to selectively produce ethanol.

Such processes do not provide significant amounts of C$_4$ products, which are but a minor and incidental by-product of the reactions involved.

SUMMARY OF THE INVENTION

A process and catalyst system has now been discovered for selective formation of C$_4$ compounds comprising n-butanol and n-butanal from methanol, hydrogen and carbon monoxide, wherein the molar amount of C$_4$ product can exceed the total amount of ethanol produced. The process of the present invention comprises reacting methanol with hydrogen and carbon monoxide in the presence of a cobalt catalyst selected from the group consisting of (a) a cobalt carbonyl, (b) a hydrido cobalt carbonyl and (c) a cobalt-containing material convertible to a cobalt carbonyl or a hydrido cobalt carbonyl, an iodine compound and an organic sulfide having the formula:

$$R_1-S-R_2$$

wherein R$_1$ and R$_2$ can be the same or different members selected from the group consisting of saturated or unsaturated, straight or branched chain alkyl radicals having from one to 24 carbon atoms, cycloalkyl radicals having from three to 40 carbon atoms, aryl radicals having from six to 20 carbon atoms, aralkyl and alkaryl radicals having from six to 40 carbon atoms and halogen substituted derivatives thereof. In order to render the present catalyst system highly selective to C$_4$ products, the molar ratio of the cobalt catalyst to the organic sulfide should be in the range of between about 2:1 and about 1:10 based upon elemental cobalt and sulfur. The reactants are subjected to elevated temperature and elevated pressure for a time sufficient to convert the methanol to significant quantities of n-butanol and n-butanal. Suprisingly, the catalyst system of the present invention can be highly selective to the formation of C$_4$ products from methanol, hydrogen and carbon monoxide when the cobalt to sulfur ratio is within the aforesaid range.

DESCRIPTION OF THE PREFERRED EMBODIMENTS

The process of the present invention comprises contacting methanol, hydrogen and carbon monoxide with a cobalt catalyst, an iodine promoter and an organic sulfide under reaction conditions for a time sufficient to convert the methanol to the desired n-butanol and n-butanal. Although hydrogen and carbon monoxide are employed herein for reaction with methanol to produce the C$_4$ products, it is understood that any combination of compounds that will form hydrogen and carbon monoxide in the reaction zone can also be used. Thus, compounds of reaction mixtures which give rise to the formation of carbon monoxide and hydrogen under the reaction conditions defined herein can be used instead of mixtures comprising carbon monoxide and hydrogen which are used in the preferred embodiments of this invention. For example, mixtures of hydrogen and carbon dioxide, water and carbon monoxide, etc., can be employed.

The mixture of hydrogen and carbon monoxide used herein can be produced from any source containing carbon and hydrogen. Two types of reactions, for example, can be used for the production of synthesis gas, i.e., partial oxidation and steam reforming. Steam reforming is the more important process when natural gas (methane) is the hydrogen-carbon source. Partial oxidation is used primarily for heavy fuel and residual oil.

The relative amounts of carbon monoxide and hydrogen employed can be varied over a wide range. However, in general, the molar ratio range of carbon monoxide to hydrogen is from about 1:10 to about 10:1, especially from about 1:3 to about 3:1. However, conventional synthesis gas (mixtures of carbon monoxide and hydrogen) with a molar ratio of about 1:1 is convenient and satisfactory for the process of the present invention. It is to be noted that molar ratios outside the aforestated ratio ranges can be employed.

The cobalt catalyst of the present invention can be a cobalt carbonyl, a hydrido cobalt carbonyl or a cobalt-containing material convertible to a cobalt carbonyl or a hydrido cobalt carbonyl. The term "cobalt carbonyl" as used in this application is a compound containing only cobalt and carbon monoxide, such as $Co_2(CO)_8$ or $Co_4(CO)_{12}$. The term "hydrido cobalt carbonyl" as used here is a compound containing only cobalt, carbon monoxide and hydrogen, such as $HCo(CO)_4$. The expression "cobalt-containing material convertible to a cobalt carbonyl or a hydrido cobalt carbonyl" includes any material which when mixed with hexane and then subjected to 4000 pounds per square inch gauge (27.6 MPa) in an atmosphere containing hydrogen and carbon monoxide in a ratio of 1:1 at 150° C. to 200° C. for a period of three hours will result in the formation of a cobalt carbonyl, a hydrido cobalt carbonyl or mixtures thereof.

Specific examples of such cobalt-containing material convertible to a cobalt carbonyl or a hydrido cobalt carbonyl include cobalt acetylacetonate, cobalt(II) sulfate, cobalt oxide ($Co_3O_4$), cobalt(II) tetrafluoroborate, cobalt(II) acetate, cobalt(II) oxalate, cobalt(II) propionate, cobalt(II) octoate, cobalt(II) butyrate, cobalt(II) benzoate, cobalt(II) valerate, cobalt(II) formate, cobalt(II) cyclohexanebutyrate, cobalt(II) 2-ethylhexaoate, cobalt(II) gluconate, cobalt(II) lactate, cobalt(II) naphthenate, cobalt(II) oleate and cobalt(II) citrate.

Any source of iodine which is capable of disassociating, that is, ionizing to form free iodide ions in the reaction medium, can be used as a promoter in the catalyst system used in the process of the present invention. Illustrative examples of iodine compounds suitable for use herein include iodine, potassium iodide, calcium iodide, sodium iodide, lithium iodide, hydrogen iodide, methyl iodide, ethyl iodide, mixtures thereof and the like.

The organic sulfide component of this invention has the formula:

$$R_1-S-R_2$$

wherein $R_1$ and $R_2$ are either the same or different members selected from the group consisting of saturated or unsaturated, straight or branched chain alkyl radicals having from one to 24 carbon atoms, preferably from one to 10 carbon atoms; cycloalkyl radicals having from three to 40 carbon atoms, preferably from three to 30 carbon atoms; aryl radicals having from six to 20 carbon atoms, preferably from six to 10 carbon atoms; aralkyl and alkaryl radicals having from six to 40 carbon atoms, preferably from six to 30 carbon atoms; and halogen substituted, particularly chlorine substituted, derivatives thereof.

The organic sulfide component is essential to the success of the present process and contributes to the selectivity of the reaction in producing a product in which the mole percent $C_4$ components exceeds that of ethanol. Suitable organic sulfide compounds for use in the present process include:

diphenyl sulfide
ditolyl sulfide
di(pentafluorophenyl) sulfide
di(pentachlorophenyl) sulfide
di(pentabromophenyl) sulfide
(pentafluorophenyl) phenyl sulfide
di(p-fluorophenyl) sulfide
di(m-fluorophenyl) sulfide
di(o-fluorophenyl) sulfide
di-(2-naphthalyl)sulfide
di-(1-naphthalyl)sulfide
di-(2-anthracenyl)sulfide
di-(1-anthracenyl)sulfide
methyl vinyl sulfide
ethyl vinyl sulfide
n-butyl vinyl sulfide
di-(1-but-2-enyl)sulfide
di-(2-but-2-enyl)sulfide
di-(n-dodecyl)sulfide
di(p-chlorophenyl) sulfide
di(m-chlorophenyl) sulfide
di(o-chlorophenyl) sulfide
di(p-methoxyphenyl) sulfide
di(m-methoxyphenyl) sulfide
di(o-methoxyphenyl) sulfide
di(p-bromophenyl) sulfide
di(m-bromophenyl) sulfide
di(o-bromophenyl) sulfide
(p-fluorophenyl)(p-chlorophenyl) sulfide
dimethyl sulfide
diethyl sulfide
dibenzyl sulfide
di-isopropyl sulfide
di-n-propyl sulfide
di-n-butyl sulfide
di-t-butyl sulfide
di-sec butyl sulfide
di-n-hexyl sulfide
di-cyclohexyl sulfide
di-2-ethylhexyl sulfide
di-1,1,1-trifluoroethyl sulfide
di-perfluorobutyl sulfide
di-1-chloropropyl sulfide
methylphenyl sulfide
ethyltolyl sulfide
ethylmethyl sulfide
t-butylethyl sulfide
phenyltolyl sulfide
(pentafluorophenyl)propyl sulfide
cyclohexyl(o-chlorophenyl) sulfide
eicosyl(p-cumyl) sulfide, etc.

The ratio of the cobalt catalyst to organic sulfide used in the reaction is vital in order to achieve large amounts of $C_4$ product and correspondingly reduce the ethanol yield. Thus, in order to provide a highly selective catalyst system, the cobalt catalyst and the organic sulfide are utilized in molar ratios, based on the elements cobalt and sulfur, in a ratio of cobalt to sulfur of from about 2:1 to about 1:10, preferably about 2:1 to about 1:2. The cobalt catalyst and the iodine promoter are introduced into the reaction zone in molar ratios, based on the elements cobalt and iodine, in a ratio of cobalt to iodine ranging from about 3:1 to about 1:10, preferably about 2:1 to about 1:4. Based on the weight of methanol introduced into the system, the weight percent of combined cobalt, sulfur and iodine can range from about 0.005 to about 25 percent, preferably from about 0.01 to about 10 percent.

The process can be carried out either in a batch operation or by passing the reactants continuously through the reactor. In each case the reactor is provided with agitation means and the pressure is maintained therein by the addition of hydrogen and carbon monoxide as required. In order to facilitate introduction of the cobalt, sulfur and iodine entities into the reaction zone and/or to facilitate recovery of the components of the reaction herein, they can be dissolved in an inert solvent, such as ethylene glycol, diethylene glycol monomethyl ether, acetone, sulfolanes, lactones, etc.

In the reaction zone the reactants are maintained at elevated temperature and elevated pressure for a time sufficient to convert the methanol to a product in which the mole percent of the combined $C_4$ products (n-butanol and n-butanal) exceeds that of ethanol. Pressures which are suitable for use in the present process generally are in the range of about 1000 to about 6000 pounds per square inch gauge (about 6.83 to about 40.98 MPa), preferably about 2000 to about 5000 pounds per square inch gauge (about 13.66 to about 34.15 MPa). Temperatures which are suitable for use in the present process are those temperatures which initiate a reaction between the reactants to selectively produce the desired $C_4$ products, and are generally from about 150° to about 250° C., preferably from about 175° to about 225° C. The reaction is conducted for a time period sufficient to convert methanol to $C_4$ products, normally from about 0.5 hour to about 10 hours, preferably from about one to about five hours.

Recovery of the $C_4$ products from the reaction product can be effected in any convenient or conventional manner, for example, by distillation. At ambient pressure and about 21° C., the components will distill off in the following sequence for the desired recovery of the $C_4$ products and any other compounds for which recovery is desired: dimethyl ether, acetaldehyde, methyl acetate, methanol, n-butanal, ethanol and n-butanol.

The following examples illustrate the process and catalyst system of the present invention. The percentages are by weight.

EXAMPLES I-III

Three millimoles of cobalt acetylacetonate, 1.5 millimoles of iodine and 100 milliliters of methanol were charged into a 300 cc. stainless steel autoclave. The reactor was next purged twice with nitrogen gas and then pressured with synthesis gas ($H_2$:CO=1) to a pressure of about 1000 pounds per square inch gauge (6.83 MPa) lower than the desired working pressure. The system was then heated to a temperature of about 200° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter and a gas sample was taken for a mass spectral analysis and the liquid product was analyzed using a Model 900 Perkin-Elmer gas chromatograph utilizing a 16-foot (4.88 meters)×⅛ inch (0.32 centimeter) stainless steel column wherein eight feet (2.44 meters) of the column was packed with 80/100 mesh Poropak Q and the other eight feet (2.44 meters) was packed with 80/100 mesh Poropak R. Poropak Q and Poropak R are polyvinyl benzene-type resins which are marketed commercially by Waters Associates, a corporation located in Milford, Massachusetts. The gas chromatograph was programmed to increase from 40° C. to 190° C. at a rate of 32° C./minute and with a helium flow rate of 30 cc./minute.

The aforesaid procedure was repeated except that 0.5 millimole of diphenyl sulfide was charged to the autoclave along with the cobalt acetylacetonate, iodine and methanol. The procedure was then repeated once again, except that three millimoles of diphenyl sulfide instead of 0.5 millimoles were charged to the autoclave along with the cobalt acetylacetonate, iodine and methanol.

The data obtained are summarized in Table I below:

TABLE I

| Example No. | I | II | III |
|---|---|---|---|
| Cobalt to Sulfur (Molar Ratio) | — | 6:1 | 1:1 |
| Iodine to Cobalt (Molar Ratio) | 1:2 | 1:2 | 1:2 |
| Methanol Converted, Mole % | 70.9 | 63.9 | 45.7 |
| Selectivity, Mole % | | | |
| Dimethyl Ether | 6.1 | 6.5 | 13.2 |
| Acetaldehyde | 21.8 | 20.7 | 28.3 |
| Ethanol | 45.2 | 41.5 | 15.5 |
| Methylacetate | 17.3 | 18.8 | 13.4 |
| n-Butanal | 4.2 | 4.3 | 11.2 |
| n-Butanol | none | 2.3 | 14.9 |
| Others* | 5.4 | 5.9 | 3.5 |
| Total Normal $C_4$ Product | 4.2 | 6.6 | 26.1 |

*This comprises, for example, methane, 1-propanol, ethylacetate, methylformate, propanal and acetals.

The results in Table I show that the addition of the organic sulfide to the catalyst system in a sufficient amount relative to the cobalt component provided a catalyst system highly selective to the formation of $C_4$ products from methanol, hydrogen and carbon monoxide. Thus, the results of Example I, which was conducted in the absence of the organic sulfide, show that the reaction was highly selective to the formation of ethanol (45.2%) rather than $C_4$ product (4.2%). The addition of the organic sulfide in Example II increased selectively towards the production of $C_4$ product (6.6%) resulting in the production of some n-butanol, but the reaction was still highly selective towards ethanol (41.5%). However, when the amount of organic sulfide was significantly increased (Example III), the results are surprising. Thus, the catalyst system of Example III is highly selective to the formation of $C_4$ products (26.1%), while the selectivity to ethanol is greatly reduced (15.5%).

Obviously, many modifications and variations of the invention, as hereinabove set forth, can be made without departing from the spirit and scope thereof, and therefore only such limitations should be imposed as are indicated in the appended claims.

We claim:

1. A process for selectively producing n-butanol and n-butanal, which comprises reacting methanol, hydrogen and carbon monoxide in the presence of a cobalt catalyst selected from the group consisting of (a) a cobalt carbonyl, (b) a hydrido cobalt carbonyl and (c) a cobalt-containing material convertible to a cobalt carbonyl or a hydrido cobalt carbonyl, an iodine promoter and an organic sulfide having the formula:

$$R_1-S-R_2$$

wherein $R_1$ and $R_2$ are either the same or different members selected from the group consisting of saturated or unsaturated, straight or branched chain alkyl radicals having from one to 24 carbon atoms, cycloalkyl radicals having from three to 40 carbon atoms, aryl radicals having from six to 20 carbon atoms, aralkyl and alkaryl radicals having from six to 40 carbon atoms and halogen substituted derivatives thereof, under elevated temperature and pressure conditions for a time sufficient to convert said methanol to n-butanol and n-butanal.

2. The process of claim 1 wherein the molar ratio of the cobalt catalyst and the organic sulfide is in the range of about 2:1 to about 1:10, based upon elemental cobalt and sulfur.

3. The process of claim 2 wherein the molar ratio of said cobalt catalyst to organic sulfide is in the range of about 2:1 to about 1:2 based upon elemental cobalt and sulfur.

4. The process of claim 2 wherein the organic sulfide is dimethyl sulfide, diethyl sulfide, dibenzyl sulfide, diphenyl sulfide, di-n-butyl sulfide, di-n-hexyl sulfide or di-n-dodecyl sulfide.

5. The process of claim 4 wherein the organic sulfide is diphenyl sulfide.

6. The process of claim 2 wherein the combined cobalt, sulfur and iodine present is between about 0.01 and about 10 percent based upon the weight of methanol.

7. The process of claim 2 wherein said cobalt catalyst is cobalt acetylacetonate.

8. The process of claim 2 wherein the reaction temperature is between about 150° and about 250° C.

9. The process of claim 8 wherein the reaction temperature is between about 175° and about 225° C.

10. The process of claim 2 wherein the reaction pressure is between about 1000 psig (6.83 MPa) and about 6000 psig (40.98 MPa).

11. The process of claim 10 wherein the reaction pressure is between about 2000 psig (13.66 MPa) and about 5000 psig (34.15 MPa).

12. The process of claim 2 wherein the reaction time is from about 0.5 to about 10 hours.

13. The process of claim 12 wherein the reaction time is from about 1 to about 5 hours.

14. The process of claim 2 wherein the iodine promoter is a member selected from the group consisting of iodine, calcium iodide, sodium iodide, lithium iodide, hydrogen iodide, methyl iodide and ethyl iodide, or mixtures thereof.

15. The process of claim 14 wherein the iodine promoter is iodine.

16. The process of claim 2 wherein the cobalt catalyst and iodine promoter are in a molar ratio of cobalt catalyst to iodine promoter from about 3:1 to about 1:10 based upon elemental cobalt and iodine.

* * * * *